United States Patent
Wada

(10) Patent No.: US 11,517,594 B2
(45) Date of Patent: Dec. 6, 2022

(54) METHODS FOR PRODUCING COMPOSITIONS CONTAINING PLASMALOGEN

(71) Applicant: NIHON PHARMACEUTICAL CO., LTD., Tokyo (JP)

(72) Inventor: Tatsuya Wada, Tokyo (JP)

(73) Assignee: NIHON PHARMACEUTICAL CO., LTD., Tokyo (JP)

( * ) Notice: Subject to any disclaimer, the term of this patent is extended or adjusted under 35 U.S.C. 154(b) by 194 days.

(21) Appl. No.: 16/978,483

(22) PCT Filed: Aug. 21, 2018

(86) PCT No.: PCT/JP2018/030759
§ 371 (c)(1),
(2) Date: Sep. 4, 2020

(87) PCT Pub. No.: WO2019/171619
PCT Pub. Date: Sep. 12, 2019

(65) Prior Publication Data
US 2021/0052667 A1 Feb. 25, 2021

(30) Foreign Application Priority Data
Mar. 8, 2018 (JP) .............................. JP2018-042155

(51) Int. Cl.
*A61K 35/616* (2015.01)
*A23L 33/10* (2016.01)
*A61K 31/685* (2006.01)

(52) U.S. Cl.
CPC ............ *A61K 35/616* (2013.01); *A23L 33/10* (2016.08); *A61K 31/685* (2013.01)

(58) Field of Classification Search
None
See application file for complete search history.

(56) References Cited

U.S. PATENT DOCUMENTS

| | | |
|---|---|---|
| 2012/0283223 A1 | 11/2012 | Ifuku et al. |
| 2013/0172293 A1 | 7/2013 | Mawatari et al. |
| 2018/0127680 A1 | 5/2018 | Fujino et al. |

FOREIGN PATENT DOCUMENTS

| | | | |
|---|---|---|---|
| JP | 61-227790 A | | 10/1986 |
| JP | WO 2008/146942 | * | 12/2008 |
| JP | 2009 9263518 | * | 11/2009 |
| JP | 2017 137439 | * | 8/2017 |
| JP | 2017-137439 A | | 8/2017 |
| WO | WO 2008/146942 A1 | | 12/2008 |
| WO | WO 2010/047404 A1 | | 4/2010 |
| WO | WO 2011/083827 A1 | | 7/2011 |
| WO | WO 2012/039472 A1 | | 3/2012 |
| WO | WO 2016/181491 A1 | | 11/2016 |

OTHER PUBLICATIONS

Chen Q. et al. Mechanism of Phospholipid Hydrolysis for Oyster *Crassostrea plicatula* Phospholipids During Storage . . . Lipids 52(12) 1045-1058, Oct. 2017. (Year: 2017).*
Berry, K. et al. Free Radical Oxidation of Plasmalogen Glycerophosphocholine Containing Esterified Docosahexaenoic Acid. Antioxidants & Redox Signaling 7(1-2)157-169 Jan.-Feb. 2005. (Year: 2005).*
International Search Report, issued in PCT/JP2018/030759, PCT/ISA/210, dated Oct. 16, 2018.
Written Opinion of the International Searching Authority, issued in PCT/JP2018/030759, PCT/ISA/237, dated Oct. 16, 2018.

* cited by examiner

*Primary Examiner* — Ralph J Gitomer
(74) *Attorney, Agent, or Firm* — Birch, Stewart, Kolasch & Birch, LLP

(57) ABSTRACT

Provided is a method for producing a composition containing plasmalogen derived from a plasmalogen-containing animal tissue, the method being without significantly decreasing an amount of plasmalogen derived the plasmalogen-containing animal tissue. A method for producing a composition containing plasmalogen derived from an animal tissue, the method comprising: (A) concentrating an alcohol extract of a plasmalogen-containing animal tissue, and (B) after diluting a concentrated product obtained by (A), allowing to stand under refrigeration.

11 Claims, No Drawings

METHODS FOR PRODUCING COMPOSITIONS CONTAINING PLASMALOGEN

TECHNICAL FIELD

The present invention relates to a method for producing a composition containing plasmalogen.

BACKGROUND ART

With regard to plasmalogen, many reports have been made regarding involvement thereof in brain signal transduction and functions thereof as an antioxidative substance in the brain. It has also been reported that the amount of plasmalogen in the brain is reduced in an Alzheimer's disease patient by about 30% as compared with that of in a healthy person. Further, it has recently been suggested that diseases associated with central nervous system inflammation, diseases associated with neurodegeneration, etc. can be treated or prevented by using a composition containing plasmalogen (Patent Documents 1 and 2).

As a method for producing plasmalogen or a composition containing the same, a method for extracting plasmalogen with an alcohol from an animal tissue containing plasmalogen (hereinafter also referred to as the "plasmalogen-containing animal tissue".) is known. For example, Patent Document 1 discloses a method of obtaining plasmalogen by concentrating an ethanol extract of a plasmalogen-containing animal tissue, adding acetone to the obtained concentrated product and centrifuging the mixture, adding a solvent to the obtained precipitate to dilute the same, and then, centrifuging the mixture.

PRIOR ART DOCUMENTS

Patent Documents

Patent Document 1: WO 2011/083827
Patent Document 2: WO 2012/039472

SUMMARY OF THE INVENTION

Problems to be Solved by the Invention

In order to produce plasmalogen or a composition containing the same on an industrial scale, the present inventor has tried to produce a composition containing plasmalogen derived from an animal tissue by concentrating an alcohol extract of the plasmalogen-containing animal tissue, adding a solvent to the obtained concentrated product to dilute the same, and then, allowing to stand the mixture at normal temperature; however, as a result, he has found that the amount of the obtainable plasmalogen was significantly reduced when it is allowed to stand at normal temperature.

Means to Solve the Problems

Accordingly, the present inventor has intensively studied in view of the above-mentioned problem, and as a result, he has found that a composition containing plasmalogen derived from an animal tissue can be produced without significantly reducing the amount of the obtainable plasmalogen when an alcohol extract of the plasmalogen-containing animal tissue is concentrated and after diluting the obtained concentrate, it is allowed to stand under refrigeration but not allowed to stand under normal temperature, whereby the present invention has been completed.

In summary, the present invention is to provide the following:

[1] A method for producing a composition containing plasmalogen derived from an animal tissue, the method comprising:
(A) concentrating an alcohol extract of a plasmalogen-containing animal tissue, and
(B) after diluting a concentrated product obtained by (A), allowing to stand under refrigeration.
[2] The method described in [1], wherein allowing to stand under refrigeration of (B) is carried out at 2 to 15° C.
[3] The method described in [1] or [2], wherein allowing to stand under refrigeration of (B) is carried out for 1 to 7 days.
[4] The method described in any of [1] to [3], wherein the plasmalogen-containing animal tissue is a dried material.
[5] The method described in [4], wherein the drying is carried out by blowing air at 25 to 59° C. to the animal tissue.
[6] The method described in any of [1] to [5], wherein the animal tissue is derived from aquatic invertebrates.
[7] The method described in [6], wherein the aquatic invertebrates are aquatic invertebrates of phylum *Chordata*, subphylum *Urochordata*, class Ascidiacea.
[8] The method described in [7], wherein the aquatic invertebrates of the phylum *Chordata*, subphylum *Urochordata*, class Ascidiacea are aquatic invertebrates of the genus *Halocynthia*.
[9] The method described in [8], wherein the aquatic invertebrates of the genus *Halocynthia* are *Halocynthia roretzi* or *Halocynthia aurantium*.
[10] The method described in any of [1] to [9], wherein plasmalogen derived from an animal tissue contains a group corresponding to an aliphatic hydrocarbon portion of docosahexaenoic acid or eicosapentaenoic acid.
[11] The method described in any of [1] to [10], wherein the composition is a food composition or a pharmaceutical composition.
[12] The method described in [11], wherein the composition is a food composition.
[13] The method described in [12], wherein the food composition is a food with function claims or a food for specified health uses, or a health food other than these.

Effects of the Invention

Among a method for producing plasmalogen, the method comprising alcohol extraction, the present invention can produce a composition containing plasmalogen derived from an animal tissue without significantly reducing the amount of obtainable plasmalogen.

Embodiments to Carry Out the Invention

In one embodiment of the present invention, provided is a method for producing a composition containing plasmalogen derived from an animal tissue, the method comprising:
(A) concentrating an alcohol extract of a plasmalogen-containing animal tissue, and
(B) after diluting a concentrated product obtained by (A), allowing to stand under refrigeration.

"Plasmalogen" is a glycerophospholipid generally having a long-chain alkenyl group via a vinyl ether bond at the 1-position (sn-1 position) of a glycerol skeleton, and for example, can be represented by the following general formula.

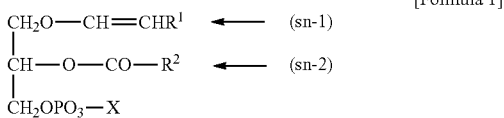

[Formula 1]

R[1] is an aliphatic hydrocarbon group, and is generally an aliphatic hydrocarbon group having 1 to 20 carbon atoms. R[1] includes, but not limited to, for example, a dodecyl group, a tetradecyl group, a hexadecyl group, an octadecyl group, an eicosanyl group.

R[2] is an aliphatic hydrocarbon group, and is generally a group corresponding to an aliphatic hydrocarbon portion of a fatty acid. R[2] includes, but not limited to, for example, a group corresponding to an aliphatic hydrocarbon portion of a fatty acid such as octadecadienoic acid, octadecatrienoic acid, eicosatetraenoic acid, eicosapentaenoic acid, docosatetraenoic acid, docosapentaenoic acid, docosahexaenoic acid.

X represents a polar group, and includes, but not limited to, for example, $-CH_2CH_2N^+H_3$, $-CH_2CH_2N^+(CH_3)_3$, $-CH_2CH(NH_2)COOH$.

"Plasmalogen-containing animal tissue" used in the present specification is not particularly limited as long as it is an animal tissue containing plasmalogen; and may be an entire animal, may be a tissue isolated from an animal such as muscle tissue, adipose tissue, nerve tissue, visceral tissue, skin tissue, egg, outer shell, blood of the animal, or may be a combination of an entire animal and an isolated tissue or a mixture of a plurality of isolated tissues. The plasmalogen-containing animal tissue includes, for example, materials derived from land vertebrates (provided that human is excluded) such as cattle, pig, horse, sheep, goat, chicken, duck; aquatic vertebrates such as bluefin tuna, salmon, saury, bonito, sardine, cod; aquatic invertebrates such as *Halocynthia roretzi*, *Halocynthia aurantium*, *Asterias amurensis*, *Asterina pectinifera*, *Strongylocentrotus nudus*, *Hemicentrotus pulcherrimus*, sea cucumber, *Anthopleura fuscoviridis* Carlgren, *Anthopleura uchidai*, scallop, *Acanthopleura japonica*, *Reishia bronni*, *Nucella freycineti*, *Chlorostoma lischkei*, *Tugali gigas*, *Mytilus galloprovincialis*, *Septifer virgatus*, *Crassostrea gigas*, octopus, squid, crab, shrimp. These may be used as whole individuals or may be used as an isolated tissue, and these may be used one kind alone or may be used in combination of two or more kinds.

The "alcohol extract of a (the) plasmalogen-containing animal tissue" in the above-mentioned (A) is not particularly limited as long as it is a liquid in which the plasmalogen-containing animal tissue is extracted with a solvent containing an alcohol.

The "solvent containing an alcohol" may be a solvent comprising an alcohol alone, or may be a mixed solvent of an alcohol and other solvent(s).

The "alcohol" to be used for extraction includes, but not limited to, for example, a primary alcohol such as methanol, ethanol, propanol, 1-butanol; a secondary alcohol such as isopropanol, 2-butanol; a tertiary alcohol such as tert-butanol. These may be used alone or may be used in combination of two or more kinds. Among these, ethanol is preferable for such alcohol since it is suitable for a food composition or a pharmaceutical composition.

The "other solvent(s)" to be used in combination with the alcohol includes, but not limited to, for example, water (for example, common water, natural water, tap water, hard water, soft water, ion-exchanged water, purified water, sterilized water; and these may be used alone or may be used in combination of two or more kinds); a fatty acid such as acetic acid, propanoic acid, butanoic acid, pentanoic acid, hexanoic acid, heptanoic acid, octanoic acid, nonanoic acid, oleic acid, or an ester thereof; and a hydrophilic organic solvent other than the above such as acetone; a hydrophobic organic solvent such as chloroform, hexane, heptane, cyclohexane, petroleum ether. These may be used alone, or may be used in combination of two or more kinds. Among these, water is preferable for such other solvent(s) to be used in combination with the alcohol, since it is suitable for a food composition or a pharmaceutical composition.

When a mixed solvent of the alcohol and the other solvent(s) is used, a mixing ratio of the alcohol and the other solvent(s) is not particularly limited as long as the object of the present invention can be accomplished. For example, the ratio of the alcohol:the other solvent(s) is generally 99.9:0.1 to 0.1:99.9, preferably 99:1 to 50:50, more preferably 99:1 to 60:40, and further more preferably 99:1 to 90:10, in volume %.

An amount of the solvent containing an alcohol to be used for obtaining an extract is not particularly limited as long as the object of the present invention can be accomplished. For example, it is, based on 1 kg of the plasmalogen-containing animal tissue, preferably about 1 to 100 L, more preferably about 3 to 50 L, further preferably about 5 to 20 L, and even more preferably about 5 to 10 L.

The method for obtaining the "alcohol extract of the plasmalogen-containing animal tissue" in the above-mentioned (A) is not particularly limited, and for example, it can be obtained as described below.

A plasmalogen-containing animal tissue is subjected to the extraction in a solvent containing an alcohol by for example, allowing to stand, mixing, or stirring, at about 1 to 50° C., preferably at about 20 to 50° C., more preferably at about 40 to 50° C., for about 0.5 to 24 hours, preferably for about 1 to 10 hours, more preferably for about 2 to 6 hours. Solids and liquids are separated, for example using a strainer, into a solid phase 1 and a liquid phase 1. Filtering the liquid phase 1 by a method such as suction filtration to remove the solid material, to obtain a liquid phase 2, which is used as an alcohol extract.

Alternatively, the following may be applied in order to heighten extraction efficiency: A solvent containing an alcohol is added to the above-separated solid phase 1. After immersion at about 1 to 50° C., preferably at about 20 to 50° C., more preferably at about 40 to 50° C., for about 0.5 to 24 hours, preferably for about 1 to 10 hours, more preferably for about 2 to 6 hours, solids and liquids are separated, for example using a strainer, into a solid phase 2 and a liquid phase 3. Filtering the liquid phase 3 by a method such as suction filtration to remove the solid material, to obtain a liquid phase 4. Combined material of the liquid phase 2 and the liquid phase 4 can be used as an alcohol extract.

Alternatively, combined material of the following can be used as an alcohol extract: one or more liquid phases obtained by further repeating re-extraction from solid phases using a solvent containing an alcohol; and the above-mentioned liquid phases 2 and 4.

Concentration of the alcohol extract in the above-mentioned (A) is not particularly limited, and may be carried out in an open system or in a closed system. It is preferably carried out in a closed system. This concentration can be carried out, for example, by reducing pressure, heating, freezing, using such as a membrane, preferably by reducing pressure. Also, this concentration is preferably carried out under bubbling with an inert gas such as nitrogen, argon, in order to prevent oxidation. When concentration is carried out by reducing pressure, it is carried out generally at a temperature of about 10 to 55° C., preferably at about 25 to 50° C., more preferably at about 40 to 50° C., and generally for about 1 to 72 hours, preferably about 6 to 48 hours, more preferably about 12 to 36 hours. A degree of pressure reduction may be, for example, about 60 mmHg.

In the above-mentioned (B), the solvent to be used for diluting the concentrated product obtained in the above-mentioned (A) is not particularly limited as long as the object of the present invention can be accomplished. Such solvent includes, for example water (for example, common water, natural water, tap water, hard water, soft water, ion-exchanged water, purified water, sterilized water; and these may be used alone or may be used in combination of two or more kinds); an alcohol such as methanol, ethanol, propanol, 1-butanol, isopropanol, 2-butanol, tert-butanol; a fatty acid such as acetic acid, propanoic acid, butanoic acid, pentanoic acid, hexanoic acid, heptanoic acid, octanoic acid, nonanoic acid, oleic acid, or an ester thereof; a hydrophilic organic solvent other than the above such as acetone; a hydrophobic organic solvent such as chloroform, hexane, heptane, cyclohexane, petroleum ether. These may be used alone, or may be used in combination of two or more kinds. Among these, the solvent to be used for diluting is preferably water or an alcohol (more preferably water or ethanol, and further more preferably water) since it is suitable for a food composition or a pharmaceutical composition.

When water is used for diluting, pH of water may be adjusted using pH adjusting agents, if necessary.

The pH adjusting agents to be used for adjusting pH of water include, but not limited to, for example, acetic acid, lactic acid, tartaric acid, oxalic acid, glycolic acid, malic acid, citric acid, succinic acid, fumaric acid, phosphoric acid, hydrochloric acid, oxalic acid, sulfuric acid, nitric acid, and salts thereof; sodium hydroxide, potassium hydroxide, sodium hydrogen carbonate, potassium carbonate. These may be used alone or may be used in combination of two or more kinds.

An amount of the solvents to be used for diluting is not particularly limited as long as the object of the present invention can be accomplished. For example, the amount is, based on 1 kg of the concentrated product obtained in the above-mentioned (A), preferably about 1 to 100 L, more preferably about 10 to 80 L, and even more preferably about 20 to 60 L.

Allowing to stand under refrigeration in the above-mentioned (B) is preferably carried out at about 2 to 15° C., more preferably carried out at about 2 to 10° C., and further more preferably carried out at about 2 to 5° C. If the temperature of allowing to stand under refrigeration is lower than 2° C., liquid phase(s) may be frozen, and if it exceeds 15° C., an amount of obtainable plasmalogen may be significantly reduced.

Allowing to stand under refrigeration in the above-mentioned (B) is preferably carried out for about 1 to 7 days, more preferably for about 2 to 6 days, further more preferably for about 3 to 5 days, and even further more preferably for about 3 days.

The concentrated product obtained in the above-mentioned (A) may be allowed to stand or store before diluting it in the above-mentioned (B). The standing or storage herein may be carried out at about 2 to 15° C., preferably at about 2 to 10° C., more preferably at about 2 to 5° C., and for about 1 to 14 days. The standing or storage herein may be carried out in an open system or in a closed system, preferably carried out in a closed system. Also, the standing or storage herein is preferably carried out under bubbling with an inert gas such as nitrogen, argon, in order to prevent oxidation of the concentrated product obtained.

In addition, a material, purified by a method such as solvent extraction and further concentrated by a method such as filtration under reduced pressure if necessary before diluting at the above-mentioned (B) the concentrated product obtained in the above-mentioned (A), may be used as a "concentrated product" in the above-mentioned (B).

In a preferred embodiment of the present invention, the plasmalogen-containing animal tissue is a dried material. The drying herein is not particularly limited, and for example, known methods such as drying by applying air, drying by dehumidification, vacuum drying, freeze drying can be used. Among these, drying by applying air is preferable.

As the drying by applying air, drying by applying air of generally about 25 to 59° C., preferably about 35 to 55° C., more preferably about 40 to 50° C. to the plasmalogen-containing animal tissue is preferable. The drying by applying air may be carried out in an open system or in a closed system. In the case of the open system, an ambient temperature is generally about 20 to 55° C., preferably about 30 to 45° C., more preferably about 35 to 40° C. In the case of the closed system, an ambient temperature is generally substantially the same as the temperature of the air to be applied to the plasmalogen-containing animal tissue.

The drying by applying air can be carried out generally for about 0.5 to 96 hours, preferably for about 1 to 72 hours, more preferably for about 6 to 48 hours, and further more preferably for about 12 to 36 hours.

A water content in the dried plasmalogen-containing animal tissue is, based on the whole amount of the plasmalogen-containing animal tissue, generally about 1 to 40% by mass, preferably about 5 to 30% by mass, and more preferably may be about 10 to 25% by mass.

The plasmalogen-containing animal tissue may be divided into two or more parts in order to enhance efficiency of the above-mentioned drying or efficiency of alcohol extraction.

In a preferred embodiment of the present invention, the animal tissue is derived from aquatic invertebrates, and is preferably aquatic invertebrates of phylum *Chordata*, subphylum *Urochordata*.

The aquatic invertebrates of the phylum *Chordata*, subphylum *Urochordata* is, for example, aquatic invertebrates such as phylum *Chordata*, subphylum *Urochordata*, class Ascidiacea; phylum *Chordata*, subphylum *Urochordata*, class Thaliacea; phylum *Chordata*, subphylum *Urochordata*, class Appendiculata.

In a further preferred embodiment of the present invention, the aquatic invertebrates are aquatic invertebrates of the phylum *Chordata*, subphylum *Urochordata*, class Ascidiacea.

In an even more preferred embodiment of the present invention, the aquatic invertebrates of the phylum *Chordata*, subphylum *Urochordata*, Ascidiacea are aquatic invertebrates of a genus *Halocynthia*. A preferred aquatic invertebrates of the genus *Halocynthia* are *Halocynthia roretzi* or *Halocynthia aurantium*.

Plasmalogen derived from an animal tissue obtainable by the present invention preferably contains a group corresponding to an aliphatic hydrocarbon of docosahexaenoic acid or eicosapentaenoic acid that is said to be effective in improving memory. Plasmalogen derived from *Halocynthia roretzi* or *Halocynthia aurantium* contains a group corresponding to an aliphatic hydrocarbon portion of docosahexaenoic acid or eicosapentaenoic acid, so that these are particularly useful.

After the above-mentioned (B), a fraction containing plasmalogen derived from the plasmalogen-containing animal tissue can be obtained by for example, removing unnecessary fraction by subjecting to a decantation at about 2 to 15° C. The fraction containing plasmalogen may be an upper layer, a lower layer, or an intermediate layer other than the above, depending on the kind of the solvent to be used for diluting. In a case of using a typical solvent, the fraction containing plasmalogen is a lower layer (preferably the liquid phase which is in the lower layer).

A composition obtained after the above-mentioned (B) may be used directly as a composition containing plasmalogen derived from an animal tissue; or a material from which unnecessary fractions are removed may be used as a composition containing plasmalogen derived from an animal tissue; or a material optionally dissolved, dispersed or suspended in a solvent may be used as a composition containing plasmalogen derived from an animal tissue. Alternatively, a material obtained by adding a solvent and by subjecting to a further treatment such as concentration, purification may be used as a composition containing plasmalogen derived from an animal tissue. The concentration herein is not particularly limited, and may be carried out in an open system or in a closed system, preferably in a closed system. This concentration can be carried out, for example by reducing pressure, heating, freezing, using such as a membrane, and among these, concentration by reducing pressure is preferable. Also, this concentration is preferably carried out under bubbling with an inert gas such as nitrogen, argon, in order to prevent oxidation of the composition. When concentration is carried out by reducing pressure, it is carried out generally at a temperature of about 10 to 55° C., preferably at about 25 to 50° C., more preferably at about 40 to 50° C., and generally for about 1 to 72 hours, preferably for about 6 to 48 hours, more preferably for about 12 to 36 hours. A degree of pressure reduction is, for example, about 60 mmHg. The purification herein includes, but not limited to, for example, solvent extraction; and chromatography such as thin layer chromatography, high performance liquid chromatography.

A desired additive(s) may be added, if necessary, during the above-mentioned (A) or (B) or treatment other than these, or to the composition obtained, and an object of adding the additive(s) is not particularly limited. For example, addition of antioxidants for the purpose of preventing oxidation of plasmalogen derived from the plasmalogen-containing animal tissue, addition of preservatives for the purpose of preserving the composition containing plasmalogen derived from an animal tissue, addition of dispersants for the purpose of homogenization of plasmalogen derived from an animal tissue. The additives that can be used include, but not limited to, for example, antioxidants such as ascorbic acid, tocopherol, erythorbic acid, sodium sulfite, dibutylhydroxytoluene, butylhydroxyanisole, catechin; preservatives such as sorbic acid, potassium sorbate, calcium sorbate, benzoic acid, sodium benzoate, propionic acid, sodium propionate, calcium propionate, sodium dehydroacetate, natamycin, pimalysin, polylysine, nisin, isopropyl paraoxybenzoate, isopropyl parahydroxybenzoate, isopropylparaben; dispersants such as polysorbates, sodium lauryl sulfate, polyoxyethylene hydrogenated castor oil, lecithin. These may be used alone or may be used in combination of two or more kinds.

The composition containing plasmalogen obtained by the present invention is preferably a food composition or a pharmaceutical composition, and particularly preferably a food composition. The food composition is preferably a food with function claims or a food for specified health uses, or a health food other than these.

Also, since plasmalogen is suggested to treat or prevent for example, diseases associated with central nervous system inflammation or diseases associated with neurodegeneration, the composition containing plasmalogen obtained by the present invention can also be a food composition or a pharmaceutical composition for treating or preventing for example, diseases associated with central nervous system inflammation or diseases associated with neurodegeneration.

The diseases associated with central nervous system inflammation include, but not limited to, for example, encephalitis, meningitis. The diseases associated with neurodegeneration include, but not limited to, for example, Alzheimer's disease, Parkinson's disease, dementia, schizophrenia, depression.

The composition containing plasmalogen obtained by the present invention can be formulated, by known or well-known methods, into preparations, for example, tablets, coated tablets, powders, granules, fine granules, hard capsules, soft capsules, pills, liquids, suspensions, emulsions, jelly, chewable tablets, soft tablets. These may be oral preparations or parenteral preparations. The preparations may contain not only plasmalogen but also other beneficial components (for example, other components having benefit to health or therapeutic) depending on its purpose.

For preparing the above-mentioned preparation, to the composition obtained by the present invention may be added, for example, excipients, binders, disintegrating agents, lubricants, sweetening agents, coloring agents, surfactants, solubilizing agents, dissolution assisting agents, preservatives, pH adjusting agents, suspending agents, isotonizing agents, buffers, analgesic agents, antioxidants.

The excipients include, but not limited to, for example, D-mannitol, lactose hydrate, crystalline cellulose, glucose, starch, sucrose, white sugar. These may be used alone or may be used in combination of two or more kinds.

The binders include, but not limited to, for example, gum Arabic, hydroxypropylmethyl cellulose, hydroxypropyl cellulose, hydroxyethyl cellulose. These may be used alone or may be used in combination of two or more kinds.

The disintegrating agents include, but not limited to, for example, corn starch, potato starch, carmellose calcium, carmellose sodium, low-substitution degree hydroxypropyl cellulose, croscarmellose sodium, crospovidone, carboxymethyl starch sodium. These may be used alone or may be used in combination of two or more kinds.

The lubricants include, but not limited to, for example, light anhydrous silicic acid, stearic acid, magnesium stearate, calcium stearate, sucrose fatty acid ester, polyethylene glycol, talc. These may be used alone or may be used in combination of two or more kinds.

The sweetening agents include, but not limited to, for example, sucrose, fructose, xylitol, sorbitol, aspartame, acesulfame potassium, sucralose. These may be used alone or may be used in combination of two or more kinds.

The coloring agents include, but not limited to, for example, yellow ferric oxide, black iron oxide, food yellow No. 4, food red No. 3, tar pigments, caramel, cacao pigments, titanium oxide, riboflavins. These may be used alone or may be used in combination of two or more kinds.

The surfactants include, but not limited to, for example, polysorbate 80, sodium lauryl sulfate, polyoxyethylene hydrogenated castor oil. These may be used alone or may be used in combination of two or more kinds.

The solubilizing agents include, but not limited to, for example, ethanol, propylene glycol, polyethylene glycol, sorbitan sesquioleate, sorbitan laurate, sorbitan palmitate, glyceryl oleate, glyceryl myristate, polyoxyethylene lauryl ether, polyoxyethylene nonylphenyl ether, glycerin. These may be used alone or may be used in combination of two or more kinds.

The dissolution assisting agents include, but not limited to, for example, polyethylene glycol; propylene glycol; cyclodextrin; sugar alcohol such as mannitol; benzyl benzoate; trisaminomethane; cholesterol; triethanolamine; sodium carbonate; sodium citrate; an alcohol such as methanol, ethanol, propanol, isopropanol; single fatty acid such as acetic acid, propanoic acid, butanoic acid, pentanoic acid, hexanoic acid, heptanoic acid, myristic acid, stearic acid, oleic acid, or an ester thereof; vegetable oil such as sesame oil, peanut oil, coconut oil, palm oil, soybean oil, olive oil, coconut oil, corn oil, cottonseed oil, castor oil, rapeseed oil, sunflower oil. These may be used alone or may be used in combination of two or more kinds.

The preservatives include, but not limited to, for example, sorbic acid, potassium sorbate, calcium sorbate, benzoic acid, sodium benzoate, propionic acid, sodium propionate, calcium propionate, sodium dehydroacetate, natamycin, pimalysin, polylysine, nisin, isopropyl paraoxybenzoate, isopropyl parahydroxybenzoate, isopropylparaben. These may be used alone or may be used in combination of two or more kinds.

The pH adjusting agents include, but not limited to, for example, acetic acid, lactic acid, tartaric acid, oxalic acid, glycolic acid, malic acid, citric acid, succinic acid, fumaric acid, phosphoric acid, hydrochloric acid, sulfuric acid, nitric acid, or salts thereof, sodium hydroxide, potassium hydroxide, sodium hydrogen carbonate, potassium carbonate. These may be used alone or may be used in combination of two or more kinds.

The suspending agents include, but not limited to, for example, stearyl triethanolamine, sodium lauryl sulfate, lauryl aminopropionic acid, lecithin, benzalkonium chloride, benzethonium chloride, glyceryl monostearate, polyvinyl alcohol, polyvinylpyrrolidone, sodium carboxymethyl cellulose, methyl cellulose, hydroxymethyl cellulose, hydroxyethyl cellulose, hydroxypropyl cellulose. These may be used alone or may be used in combination of two or more kinds.

The isotonizing agents include, but not limited to, for example, sodium chloride, glycerin, mannitol. These may be used alone or may be used in combination of two or more kinds.

The buffers include, but not limited to, for example, phosphates, acetates, carbonates, citrates, and buffer solutions containing these. These may be used alone or may be used in combination of two or more kinds.

The analgesic agents include, but not limited to, for example, benzyl alcohol.

The antioxidants include, but not limited to, for example, ascorbic acid, tocopherol, erythorbic acid, sodium sulfite, dibutylhydroxytoluene, butylhydroxyanisole, catechin. These may be used alone or may be used in combination of two or more kinds.

An amount of plasmalogen in the above-mentioned preparation is not particularly limited as long as the desired effect is exhibited, and can be appropriately set according to an amount of plasmalogen that is preferably administered per a day, the amount being preferably, for example 0.05 to 99.9% by mass, more preferably 0.1 to 80% by mass, and more further preferably 0.15 to 40% by mass, based on the total amount of the preparation.

EXAMPLES

In the following, the present invention will be explained in more detail by referring to Examples, but these Examples do not limit the scope of the present invention in any way.

Example 1, Comparative Examples 1 to 3

*Halocynthia roretzi* with shells was divided into two equal parts, and dried in a cool air dryer by applying air at about 45° C. for about 24 hours (the temperature in the cool air dryer (ambient temperature) becomes about 45° C.). To the dried material was added a mixed solution of ethanol and water (95% by volume:5% by volume), and the mixture was extracted under stirring at about 40° C. for about 2 hours. The solid and liquid were separated, using a stainless strainer (200 mesh), into a solid phase 1 and a liquid phase 1. The liquid phase 1 was subjected to suction filtration to remove the solid material, to obtain a liquid phase 2. To the solid phase 1 was added a mixed solution of ethanol and water (95% by volume:5% by volume). After immersion at room temperature for about 10 hours, the solid and liquid were separated, using a stainless strainer (200 mesh), into a solid phase 2 and a liquid phase 3. The liquid phase 3 was subjected to suction filtration to remove the solid material, to obtain a liquid phase 4. The liquid phase 2 and the liquid phase 4 were combined and concentrated under reduced pressure at about 45° C. for about 24 hours. The concentrated product was stored, under nitrogen bubbling, in a sealed condition at about 5° C. for about 8 days. Thereafter, water was added thereto to dilute the product, and the resulting material was allowed to stand at the temperature shown below for about 3 days. Thereafter, the supernatant was removed by decantation at about 4° C. to collect a liquid phase 5, and a content of plasmalogen in the liquid phase 5 was measured by high performance liquid chromatography.

TABLE 1

|  | Example 1 | Comparative Example 1 | Comparative Example 2 | Comparative Example 3 |
| --- | --- | --- | --- | --- |
| Temperature (° C.) at standing | 2~5 | 16~20 | 21~25 | 26~35 |
| Plasmalogen content (% by mass) in liquid phase | 2.46 | 1.06 | 0.76 | 0.13 |

From the results of Example 1 and Comparative Examples 1 to 3, when the standing temperature is 2 to 5° C., as compared with the temperature other than that, it can be understood that plasmalogen content derived from a plasmalogen-containing animal tissue in the liquid phase is higher.

Accordingly, the production method of Example 1 is a method which can produce a composition containing plasmalogen derived from an animal tissue without significantly reducing an amount of plasmalogen derived from a plasmalogen-containing animal tissue.

Example 2, Comparative Examples 4 to 6

*Halocynthia roretzi* with shells was divided into two equal parts, and dried in a cool air dryer by applying air at a temperature shown in the following Table for about 24 hours (the temperature in the cool air dryer (ambient temperature) becomes substantially the same as the temperature of the air in each Example or Comparative Example). To the dried material was added a mixed solution of ethanol and water (95% by volume:5% by volume), and the mixture was extracted under stirring at about 40° C. for about 2 hours. The solid and liquid were separated, using a stainless strainer (200 mesh), into a solid phase 1 and a liquid phase 1. The liquid phase 1 was subjected to suction filtration to remove the solid material, to obtain a liquid phase 2. To the solid phase 1 was added a mixed solution of ethanol and water (95% by volume:5% by volume). After immersion at room temperature for about 10 hours, the solid and liquid were separated, using a stainless strainer (200 mesh), into a solid phase 2 and a liquid phase 3. The liquid phase 3 was subjected to suction filtration to remove the solid material, to obtain a liquid phase 4. After combining the liquid phase 2 and the liquid phase 4, a content of plasmalogen in the combined liquid phases was measured by high performance liquid chromatography.

TABLE 2

|  | Example 2 | Comparative Example 4 | Comparative Example 5 | Comparative Example 6 |
|---|---|---|---|---|
| Temperature (° C.) of air | 40~50 | 60 | 85 | 100 |
| Plasmalogen content (% by mass) in extracted liquid | 0.49 | 0.21 | 0.09 | 0.02 |

It can be understood from the results of Example 2 and Comparative Examples 4 to 6 that plasmalogen content derived from a plasmalogen-containing animal tissue in the alcohol extract is higher when drying is carried out by applying air at 40 to 50° C. to an animal tissue, as compared with the conditions other than that.

Accordingly, the production method of Example 2 is a method which can produce a composition containing higher concentration of plasmalogen derived from an animal tissue.

As shown in the results of Examples mentioned above, the present invention can produce a composition containing plasmalogen derived from an animal tissue without significantly reducing an amount of plasmalogen derived from a plasmalogen-containing animal tissue.

The invention claimed is:

1. A method for producing a composition containing plasmalogen derived from an animal tissue, the method comprising:
   (A) concentrating an alcohol extract of a plasmalogen-containing animal tissue, and
   (B) diluting a concentrated product obtained by (A) to obtain a diluted product, and keeping the diluted product under refrigeration,
   wherein keeping the diluted product under refrigeration in (B) is carried out at 2 to 15° C.

2. The method according to claim 1, wherein keeping the diluted product under refrigeration of (B) is carried out for 1 to 7 days.

3. The method according to claim 1, wherein the plasmalogen-containing animal tissue is a dried material.

4. The method according to claim 3, wherein the drying is carried out by blowing air at 25 to 59° C. to the animal tissue.

5. The method according to claim 1, wherein the animal tissue is derived from aquatic invertebrates.

6. The method according to claim 5, wherein the aquatic invertebrates are aquatic invertebrates of phylum *Chordata*, subphylum *Urochordata*, class Ascidiacea.

7. The method according to claim 6, wherein the aquatic invertebrates of phylum *Chordata*, subphylum *Urochordata*, class Ascidiacea are aquatic invertebrates of the genus *Halocynthia*.

8. The method according to claim 7, wherein the aquatic invertebrates of the genus *Halocynthia* are *Halocynthia roretzi* or *Halocynthia aurantium*.

9. The method according to claim 1, wherein plasmalogen derived from an animal tissue contains a group corresponding to an aliphatic hydrocarbon portion of docosahexaenoic acid or eicosapentaenoic acid.

10. The method according to claim 1, wherein the composition is a food composition or a pharmaceutical composition.

11. The method according to claim 10, wherein the composition is a food composition.

* * * * *